United States Patent [19]

Chappell et al.

[11] Patent Number: 5,248,794
[45] Date of Patent: Sep. 28, 1993

[54] PROCESS FOR PURIFYING PROPYLENE OXIDE

[75] Inventors: Michael L. Chappell, Lake Jackson; Cameron T. Costain, Angleton, both of Tex.

[73] Assignee: The Dow Chemical Company, Midland, Mich.

[21] Appl. No.: 17,916

[22] Filed: Feb. 16, 1993

[51] Int. Cl.⁵ .................. C07D 301/32; C07D 303/04; C07C 43/13; C08G 18/00
[52] U.S. Cl. .................................... 549/541; 521/159; 549/538; 568/679
[58] Field of Search ............................... 549/541, 538

[56] References Cited

U.S. PATENT DOCUMENTS

| | | | |
|---|---|---|---|
| 4,692,535 | 9/1987 | Larson et al. | 549/542 |
| 4,704,463 | 11/1987 | Blytas | 549/541 |
| 5,107,002 | 4/1992 | Shih | 549/541 |

Primary Examiner—Joseph E. Evans

[57] ABSTRACT

A process for purifying propylene oxide containing an unacceptable quantity of a poly(propylene oxide) polymer contaminant having a molecular weight of at least about 50,000, comprising the step of filtering propylene oxide containing such polymer contaminant through one or more membranes to provide a propylene oxide product fraction having an acceptable quantity of poly(propylene oxide) polymer contaminant therein and a second fraction which is more highly concentrated in such polymer contaminant.

6 Claims, No Drawings

PROCESS FOR PURIFYING PROPYLENE OXIDE

The present invention relates generally to processes for the purification and/or separation of propylene oxide. The present invention relates more particularly to a process of the type described in U.S. Pat. No. 4,692,535 to Larson et al. (hereafter, Larson), wherein a propylene oxide product suitable as an intermediate in the production of polyether polyols for high resilient flexible polyurethane foam applications is made by removing substantially all of a high molecular weight poly(propylene oxide) fraction from an otherwise commercially-acceptable propylene oxide.

As disclosed in the Larson patent, propylene oxide of an otherwise commercially-acceptable purity was found to contain a certain nonvolatile impurity (namely, poly(propylene oxide) (or PPO) having a molecular weight of at least 50,000), which impurity made the propylene oxide unsuitable for making polyether polyols to be used with a polyisocyanate and blowing agent in the manufacture of acceptable high resilient flexible polyurethane foams. Polyether polyols prepared from propylene oxide having in excess of 0.1 parts per million by weight of the high molecular weight poly(propylene oxide) impurity were determined to lead to low foam rise and substantial blow hole formation in the polyurethane foams, whereas polyether polyols made from propylene oxide having reduced levels of the high molecular weight PPO impurity produced polyurethane foams with good foam rise and without substantial blow hole formation.

The solution proposed by Larson involved filtering or percolating either crude liquid propylene oxide of 95 percent or greater propylene oxide content or propylene oxide of otherwise commercially-acceptable, 99 percent purity or better through a fixed bed of an adsorbent material. The adsorbent materials suggested by Larson as suitable for this purpose are activated carbon, charcoal and attapulgite.

SUMMARY OF THE PRESENT INVENTION

The present invention provides, as in Larson, a process for purifying propylene oxide containing an unacceptable quantity of a poly(propylene oxide) polymer contaminant having a molecular weight of at least about 50,000. The present inventive process, however, performs this purification via membrane filtration. An advantage or attraction of the proposed membrane filtration process is that, unlike in Larson's process, there is no bed of adsorbent material to dispose of or regenerate.

"Unacceptable" and "acceptable" in the context of the present invention refer to those levels of the poly(propylene oxide) contaminant which make the polyether polyols produced from propylene oxide containing such levels of such contaminant commercially unacceptable or acceptable, respectively, for making high resilient flexible polyurethane foams.

In another, related aspect, the invention provides a process for making polyether polyols from propylene oxide, wherein the propylene oxide has been purified according to the process described in the preceding paragraph. In still another aspect, a process for making high resilient flexible polyurethane foams from the just-mentioned polyether polyols is provided.

DETAILED DESCRIPTION OF THE PREFERRED EMBODIMENTS

The process of the present invention is readily adaptable to commercial industrial operations, and involves as indicated above the removal of high molecular weight poly(propylene oxide) (having a molecular weight generally of at least 50,000, for example) from crude propylene oxide of 95 percent or greater propylene oxide content or from propylene oxide of an otherwise commercially-acceptable purity.

The purified propylene oxide is suitable for direct conversion (generally with one or more other organic oxides) to highly pure polyether polyols via reaction (normally catalyzed) with an initiator containing two or more active hydrogens. These polyols then react with an isocyanate in the presence generally of water and other conventional materials, e.g., inorganic fillers, surfactants, catalysts, auxiliary blowing agents, and provide flexible, stable polyurethane resilient foams exhibiting high rise while being substantially free of blowhole formation.

The processes of producing polyether polyols from oxides including propylene oxide and of producing high resilient flexible Polyurethane foams from such polyols are well-known in the art and are broadly summarized and described in "Flexible Polyurethane Foams", Herrington and Hock (Dow Plastics, 1991), so that no additional explanation or description need be offered herein.

The propylene oxide starting material of the purification process of the present invention may be obtained by any of the known routes for the production of propylene oxide. The purification process of the present invention is most conveniently effected at any time after propylene oxide of an otherwise suitable commercial purity has been obtained and the poly(propylene oxide) contaminant formed therein at unacceptable levels.

Preferably the inventive purification process is followed by prompt conversion of the purified propylene oxide product into the desired polyether polyols, or by shipment or storage of the purified product in a vessel which is made of a conventional carbon steel but which is kept at a low temperature (e.g., about 7 degrees Celsius) or in a vessel constructed of or lined with a suitable material (e.g., a stainless steel such as is preferably used for constructing treatment vessels for performing the present process). In this regard, conventional carbon steels were found by Larson to catalyze over a period of time at a given temperature the formation of the undesired high molecular weight poly(propylene oxide) contaminant.

The high molecular weight fraction of poly(propylene oxide) that is sought to be removed in Larson and in the instant process differs from propylene oxide on the basis of molecular size alone. Certain membranes, notably polymeric semipermeable membranes, are known to separate on the basis of molecular size; it was considered in making the present invention that it might be possible, through the use of one or more of such membranes, to separate the offending high molecular weight poly(propylene oxide) (or PPO) impurity from propylene oxide based simply on the relatively large size differential between these two materials.

Initially it is observed that propylene oxide is an aggressive solvent and will dissolve most polymeric membrane materials. Only highly crosslinked or chemically inert membranes are for this reason potentially useful in the present process, and in initial screenings membranes constructed of poly(vinylidene fluoride) or acrylonitrile have been found to possess the requisite stability for use in the process. A preferred material, based on the aforementioned initial screenings, is acrylonitrile. Other membrane materials of a fundamentally inert nature may be suitable as well and may in fact be superior to either poly(vinylidene fluoride) or acrylonitrile, but it is considered that these other materials can be selected without undue experimentation by following the initial screening process described below and utilized herein.

Membrane pore size is conventionally rated in terms of a particular membrane's molecular weight cutoff (MWCO). Conventionally the MWCO refers to the membrane's ability to reject, or hold back, a large inert molecule from an aqueous solution of the material. Molecules with molecular weights smaller than the MWCO pass through the membrane, while larger molecules are retained.

Because the intended application (separating propylene oxide (a nonaqueous solvent) from the high molecular weight poly(propylene oxide) (a reactive permeating molecule)) is very different from the described system upon which MWCO's are based and established, the MWCO's of these membranes provide only general indications of suitability in the present process. A SEPA TM RG-03 acrylonitrile membrane (Osmonics Inc.) which has a reported MWCO of 2000 has been found suitable in the initial tests, for example, for separating poly(propylene oxide) from propylene oxide. A SEPA TM AN-03 Poly(vinylidene fluoride) membrane (Osmonics Inc.) having a reported MWCO of 15,000 has also been found suitable.

In a presently-preferred embodiment of the process of the present invention, propylene oxide to be purified is filtered through one or more flat acrylonitrile membranes in plate and frame mountings. The pressure drop across a given membrane will preferably be from about 30 up to about 200 pounds per square inch, more preferably will be from about 50 to about 200 pounds per square inch, and most preferably will be about 50 pounds per square inch up to 100 pounds per square inch. The low pressure side of the membrane will preferably be at slightly greater than atmospheric pressure, e.g. about 15 to 20 pounds per square inch (absolute).

Preferably a sufficient number of membranes will be arranged in parallel to process a desired throughput, but those skilled in the art will recognize that additional membranes could be employed in series with intervening pumps to achieve greater separation (in a series of permeate membrane filtrations) or to achieve a higher permeate to feed ratio with lower separation (in a series of retentate membrane filtrations).

Operating temperatures will typically range from 20 to 25 degrees Celsius up to 35 to 40 degrees Celsius and greater, as limited by the boiling point of propylene oxide at the pressure on the low pressure side of the membrane. Membrane lifetimes will preferably be on the order of about 60 days and greater at a poly(propylene oxide) rejection rate of about 85 percent and greater, where the level of poly(propylene oxide) is measured in the feed and permeate according to the method prescribed in Example 1 below. The poly(propylene oxide) content in the permeate is reduced to acceptable levels, preferably is reduced to less than about 100 parts per billion (ppb) by weight, more preferably is reduced to less than about 65 ppb, and most preferably is reduced to less than about 50 ppb.

The permeate (purified propylene oxide) flow rate that can be expected from a given membrane area will vary based on the particular membrane employed and on the membrane's operating conditions, especially on the pressure drop across the membrane. For an acrylonitrile (SEPA TM RG-03 type) membrane operating at 35 to 40 degrees Celsius and a pressure drop of about 45 to 50 pounds per square inch (from about 15 to 20 pounds per square inch on the low pressure side up to about 65 pounds per square inch on the high pressure side), for example, the permeate flow rate over a 60 day period ranged downwardly in Example 2 below from about 7 milliliters per minute per square foot per pound per square inch (ml/min.ft$^2$.psi) to about 3 ml/min.ft$^2$.psi. Under these same circumstances, the permeate comprised from about 25 percent to about 50 percent of the total feed.

The present invention is demonstrated further in the examples which follow:

EXAMPLE 1

For this example a series of initial screening tests were performed on various polymeric semipermeable membrane samples sold by Osmonics Inc. under the SEPA TM mark. Since propylene oxide has a high vapor pressure and is highly flammable, these tests were conducted inside an explosion-proof freezer set at 0 degrees Celsius.

The apparatus employed to conduct these screening tests included a stainless steel static cell equipped with top and bottom flanges, and having a section of membrane placed on a porous Teflon TM PTFE support. A supply of an inert pressurizing gas (nitrogen) was connected to the cell via the top flange.

In operation, the static cell was initially rinsed with clean tetrahydrofuran (THF). After removing the top and bottom flanges, a membrane sample was then placed on top of the porous PTFE support with the active side up, and the membrane/support combination placed inside the bottom flange. The bottom flange was secured to the cell, and a volume of the unfiltered propylene oxide was then placed in the cell, with an outlet tube from the bottom flange being positioned over a clean THF-rinsed beaker. If no fluid dripped from the cell in two minutes, then the membrane was considered pinhole-free and the testing process was resumed. The top flange was placed on the cell, and a low nitrogen pressure applied to the cell to flush propylene oxide material through the membrane. After depressurization, the top flange was removed and any remaining propylene oxide drained from the cell and discarded.

A fresh charge of propylene oxide to be treated was then placed in the cell, the top flange replaced, and nitrogen pressure reapplied to achieve and maintain a permeate rate of 2 drops per second. As soon as the desired volume of permeate had been collected, the cell was depressurized and the retentate collected in a separate container. One or more additional charges of propylene oxide were placed in the cell, and the cell reassembled and repressurized to collect permeate in the same manner. The permeate and retentate samples were combined and analyzed for poly(propylene oxide) concentrations. Table 1 lists the membranes which were screened or tested, and the amounts flushed through the membrane initially, or added, filtered and collected as permeate or retentate.

TABLE 1

| Membrane Type (Flush Vol. in mL) | Amt. Charged (mL) | Permeate Collected (mL) | Retentate Collected (mL) |
|---|---|---|---|
| PP[a](100) | 152 | 100 | 52 |
|  | 155 | 100 | 55 |
|  | 111 | 70 | 30 |
| PP[b](90) | 150 | 70 | 80 |
|  | 170 | 90 | 80 |
| PVDF[c](100) | 200 | 100 | 100 |
|  | 200 | 100 | 100 |
| PVDF[d](90) | 190 | 100 | 90 |
|  | 200 | 100 | 100 |
| PVDF[e](100) | 210 | 115 | 95 |
|  | 215 | 100 | 115 |
| AN[f](100) | 190 | 100 | 95 |
|  | 200 | 110 | 115 |
| PS[g] | (Dissolved on flush) | | |
| PS[h] | (Dissolved on flush) | | |
| CA[i] | (Dissolved on flush) | | |

[a] Polypropylene. SEPA TM YL-01 type, 30,000 MWCO;
[b] Same as [a];
[c] Poly(vinylidene fluoride). SEPA TM AP-01. 700 MWCO;
[d] Poly(vinylidene fluoride). SEPA TM AP-01. 3,000 MWCO;
[e] Poly(vinylidene fluoride). SEPA TM AP-01. 15,000 MWCO;
[f] Acrylonitrile. SEPA TM AN-03 type. 2,000 MWCO;
[g] Polysulfone. SEPA TM HG-05 type. 2,000 MWCO;
[h] Polysulfone. SEPA TM HG-01 type. 5,000 MWCO;
[i] Cellulose Acetate. SEPA TM SG-15 type. 2,000 MWCO;

The test method employed for analyzing poly(propylene oxide) in this Example, as well as in Example 2 below, was designed to provide a quantitative indication for poly(propylene oxide) having a molecular weight of about 40,000 and higher, based on polystyrene standards (polystyrene standard kit, narrow distribution, available from Polymer Laboratories (Cat. No. 2010-0100)). The method's lower limit of detection was about 10 parts per billion by weight.

According to the test method, each of the various feed (unfiltered), permeate and retentate samples (each being 150 mL in volume, with the exception of the retentate sample collected in the screening of the first membrane listed above and for which correction was made in the analytical calculations) to be analyzed was transferred first to a clean, dry evaporating dish, which was then placed on a temperature bath in a fume hood at about 30 to 50 degrees Celsius for about 1 to 2 hours.

The evaporating dish containing any non-volatile residue was then dried in an oven at 105 to 110 degrees Celsius for about 30 minutes, and then cooled in a desiccator for another 30 minutes. The oven-dried and desiccator-cooled evaporating dish and residue were then tared on an analytical balance, and 1.5 mL of tetrahydrofuran (THF) were added with swirling to dissolve any PPO present in the residue, using a glass Petri dish as a cover to minimize evaporation. The dish was then reweighed to obtain the weight of THF left, and a 1-mL glass syringe was filled with the sample.

The sample was thereafter chromatographed on a single gel permeation chromatography (GPC) column (Ultrastyragel TM -type (Part No. 10571), 500 angstrom pore size, 300 mm long by 7.8 mm diameter, Waters Associates) under conditions maximizing sensitivity (i.e., 1.2 mL/minute eluent flowrate, 40 degrees Celsius (column and detector), injection volume of 300 pL). A pre-column filter was used (2 micrometer frit, Part No. 84560 from Waters Associates), and the injection valve was a six port unit with a 300 microliter loop.

The pore size of the column was selected such that all high molecular weight components eluted as a single peak at the column's exclusion limit of 4.8 minutes. A differential refractive index detector (Model 1047 differential refractive index detector from Hewlett-Packard Company) was then used, and quantitation performed by peak height comparison to a previously-run polyglycol (polypropylene glycol P-2000 grade, The Dow Chemical Company) standard solution (0.1 grams with THF to 100 mL, then 2 mL taken and further diluted to 100 mL with additional THF).

The concentration of PPO in parts per billion by weight was calculated as follows:

PPb of PPO = (Pk Ht, Spl) × (CSTD) × (WT-THF) × 1362 × (Pk Ht, Std) × (Vol-PO), where Pk Ht, Spl is the peak height of the sample at a given attenuation, Pk Ht, Std is the peak height of the polyglycol standard at the same attenuation, CSTD is the actual concentration of the standard in micrograms per milliliter, calculated by multiplying the actual weight of the P-2000 polyglycol used (to the nearest 0.001 grams) by 200, and Vol-PO is the volume of propylene oxide evaporated in mL.

Where the calculated concentration of high molecular weight PPO exceeded 11,000 but was less than 50,000 ppb, the analysis was repeated using 30.0 mL of propylene oxide to start. Where the calculated concentration was between 50,000 and 200,000 ppb, the starting volume of PO was reduced to 3.0 mL, and for levels of between 200,000 and 1,000,000 parts per billion the starting amount of propylene oxide was reduced to 0.3 mL.

Because this method is not specific to high molecular weight PPO, care was taken in this Example and in Example 2 below to prevent sample contamination with other high molecular weight species.

The results of the initial screenings are shown in Table 2:

TABLE 2

| Membrane Type | MWCO | PPO Concentration (ppm by weight) | | | Rejection (%) |
|---|---|---|---|---|---|
| | | F[a] | R[b] | P[c] | |
| PP[d] | 30,000 | 262 | 302 | 542 | (100) |
| PP | 30,000 | 262 | 1543 | 291 | (11) |
| PVDF[e] | 700 | 262 | 284 | 213 | 18 |
| PVDF | 3,000 | 262 | 284 | 215 | 18 |
| PVDF | 15,000 | 979 | 967 | 714 | 27 |
| AN[f] | 2,000 | 979 | 919 | 692 | 29 |

[a] Feed;
[b] Retentate;
[c] Permeate;
[d] Polypropylene, SEPA TM YL-01 type;
[e] Poly(vinylidene fluoride), SEPA TM AP-01 type;
[f] Acrylonitrile, SEPA TM AN-03 type;

The polypropylene membranes were not suitable, since propylene oxide apparently leaches out the plasticizers used in manufacturing these membranes. The polysulfone and cellulose acetate membranes (see Table 1) were obviously unsuitable as well, and so are not listed in Table 2.

The poly(vinylidene fluoride) (PVDF) and acrylonitrile (AN) membranes were able to make the desired separation. The PVDF membranes with MWCO's of 700 and 3000 were essentially indistinguishable, as were the PVDF and AN membranes having respective MWCO's of 15000 and 2000.

EXAMPLE 2

In this example, the SEPA ™ AN-03 type acrylonitrile membrane from Example 1 was installed in a ¼ square foot plate and frame membrane test unit, and tested with a continuous flow of unfiltered propylene oxide over a period of about 86 days, with a pressure drop from 65 pounds per square inch on the high side to about 16 to 18 pounds per square inch on the low pressure side of the membrane. The operating temperature was generally about 37 degrees Celsius. A shutdown occurred of the membrane unit on day 38 of the test, and the unit was started up again on day 48 of the run.

Samples of the unfiltered feed, of the retentate and permeate streams were taken on a daily basis, with the first samples being taken about 2 hours after start-up. These samples were analyzed for PPO concentrations according to the test method outlined in Example 1, using two shots of a single evaporated sample (the average of these two shots being reported). Flow rates were also measured of the permeate and retentate streams to assess membrane compaction over the duration of the test. These various measurements are shown below in Table 3, wherein PPO concentrations are given in parts per billion by weight, and flow rates are in milliliters per minute:

TABLE 3

| Day | Feed PPO (ppb) | Permeate Flow/PPO | Retentate Flow/PPO | PPO Rejection (%) |
|---|---|---|---|---|
| 1 | 153 | 90/105 | 1814/168 | 31 |
| 2 | 176 | 76/27 | 1656/182 | 85 |
| 3 | 130 | 73/31 | 1371/132 | 76 |
| 6 | 137 | 74/40 | 711/132 | 71 |
| 7 | 177 | 63/22 | 1814/184 | 88 |
| 8 | 187 | 62/16 | 1870/199 | 91 |
| 9 | 122 | 57/16 | 1738/125 | 87 |
| 10 | 114 | 60/15 | 1860/130 | 87 |
| 14 | 132 | 62/17 | 1164/135 | 87 |
| 15 | 119 | 58/16 | 1280/127 | 87 |
| 17 | 125 | 54/16 | 1650/138 | 87 |
| 21 | 274 | 58/14 | 1620/279 | 95 |
| 27 | 126 | 52/13 | 1720/143 | 90 |
| 29 | 98 | 49/9 | 1590/113 | 91 |
| 31 | 80 | 47/12 | 1650/52 | 85 |
| 34 | 145 | 47/10 | 1800/156 | 93 |
| 36 | 129 | 43/16 | 1840/150 | 88 |
| 49 | 281 | 55/30 | 1200/308 | 89 |
| 52 | 147 | 46/0 | 1920/151 | 100 |
| 55 | 108 | 48/0 | 1660/118 | 100 |
| 59 | 127 | 42/12 | 1810/123 | 91 |
| 62 | 122 | 41/12 | 1600/120 | 90 |
| 64 | 107 | 41/18 | 1820/108 | 83 |
| 69 | 108 | 41/15 | 1854/128 | 86 |
| 71 | 81 | 34/12 | 1920/142 | 85 |
| 73 | 128 | 37/23 | 2000/128 | 82 |
| 77 | 163 | 37/65 | 1920/182 | 60 |
| 78 | 184 | 39/42 | 1950/190 | 77 |
| 86 | 140 | 37/46 | 1860/122 | 67 |

The average standard deviation for the two PPO determinations with respect to any sample of feed was about 5.67 parts per billion by weight, while the average standard deviation in PPO concentration for the retentate samples was about 11 parts per billion and for the permeate was about 4.33 parts per billion. Errors in the determination of the flow rates were estimated at about 2 percent.

Considering these errors, and after an initial break-in period, it nevertheless appears that good PPO removal was achieved over approximately 60 days of operation before and after the shutdown, with some diminishment in PPO removal after that length of time. Unit flow rate through the membrane declined steadily over the test run, showing a compaction of the membrane over time.

At about day 16 of the run, a 1 gallon sample of the permeate was collected and sent to a manufacturer of polyether polyols for high resilient flexible polyurethane foam applications. A polyether polyol was prepared and the polyol thereafter made into a foam for blowhole and foam rise testing. On a scale of 1-10, with 0-1 being rated acceptable and 2-10 being unacceptable, the foam prepared from this polyol was rated a "0".

The foregoing examples demonstrate clearly the utility of the present invention. Those skilled in the art will appreciate, however, that numerous changes can be made in the embodiments which have been described and/or exemplified herein without departing in scope or spirit from the present invention, as more particularly defined by the claims below.

What is claimed is:

1. A process for purifying propylene oxide/containing an unacceptable quantity of a poly(propylene oxide) polymer contaminant having a molecular weight of at least about 50,000, comprising the step of filtering propylene oxide containing such polymer contaminant through one or more membranes to provide a propylene oxide product fraction having an acceptable quantity of poly(propylene oxide) polymer contaminant therein and a second fraction which is more highly concentrated in such polymer contaminant.

2. A process as defined in claim 1, wherein the one or more membranes are polymeric semipermeable membranes constructed of a material selected from the group consisting of poly(vinylidene fluoride) and acrylonitrile.

3. A process as defined in claim 1, wherein the pressure drop across a membrane is from about 30 to about 200 pounds per square inch.

4. A process as defined in claim 3, wherein the pressure drop is from about 50 to about 200 pounds per square inch.

5. A process as defined in claim 4, wherein the pressure drop is from about 50 pounds per square inch to about 100 pounds per square inch.

6. A process as defined in claim 1, wherein the one or more membranes are able to maintain a rejection rate of said poly(propylene oxide) polymer contaminant of at least about 85 percent for at least about 60 days.

* * * * *